United States Patent [19]

Quinlan

[11] Patent Number: 4,781,920

[45] Date of Patent: Nov. 1, 1988

[54] ANTHELMINTIC PASTE COMPOSITIONS CONTAINING RESINATES OF D1-6-PHENYL-2,3,5,6-TETRAHYDROIMIDAZO[2,1-B]THIAZOLE

[75] Inventor: James M. Quinlan, Trenton, N.J.

[73] Assignee: American Cyanamid Company, Stamford, Conn.

[21] Appl. No.: 772,097

[22] Filed: Sep. 3, 1985

Related U.S. Application Data

[63] Continuation-in-part of Ser. No. 670,839, Nov. 13, 1984, abandoned.

[51] Int. Cl.$^4$ ............................................. A61K 31/74
[52] U.S. Cl. ............................................. 424/79; 514/2; 514/21; 514/51; 514/948; 514/789; 514/970; 514/975; 514/100; 514/119; 514/116; 514/89; 514/117; 514/129; 514/157; 514/154; 514/30; 514/158; 514/472
[58] Field of Search ................ 424/88, 79; 514/2, 21, 514/57, 948, 789, 970, 975, 100, 119, 116, 89, 117, 129, 157, 154, 30, 158, 472

[56] References Cited

U.S. PATENT DOCUMENTS

| | | | |
|---|---|---|---|
| 3,053,733 | 9/1962 | Chance | 424/79 |
| 3,166,472 | 1/1965 | Menn et al. | 514/136 |
| 3,553,322 | 1/1971 | Hass et al. | 514/136 |
| 3,574,227 | 4/1971 | Lesley et al. | 424/79 |
| 3,937,825 | 2/1976 | Alford | 514/129 |
| 4,197,307 | 4/1980 | Gallay et al. | 548/329 |
| 4,414,222 | 11/1983 | Brooker et al. | 514/946 |

FOREIGN PATENT DOCUMENTS

| | | | |
|---|---|---|---|
| 0946742 | 5/1974 | Canada | 424/92 |
| 2030043 | 4/1980 | European Pat. Off. | 424/92 |
| 2475396 | 8/1981 | France | 424/92 |

*Primary Examiner*—Delbert R. Phillips
*Assistant Examiner*—Garnette D. Draper
*Attorney, Agent, or Firm*—Alice C. Brennan

[57] ABSTRACT

The invention provides physically stable anthelmintic paste compositions containing resinates of d1-6-phenyl-2,3,5,6-tetrahydroimidazo[2,1-b]thiazole and other anthelmintic compounds in combination with a wide variety of therapeutic agents such as antibiotics, vitamins, vaccines, or mineral supplements.

10 Claims, No Drawings

ANTHELMINTIC PASTE COMPOSITIONS CONTAINING RESINATES OF D1-6-PHENYL-2,3,5,6-TETRAHY-DROIMIDAZO[2,1-B]THIAZOLE

This application is a continuation-in-part of application Ser. No. 670,839, filed Nov. 13, 1984, abandoned.

SUMMARY OF THE INVENTION

The desirability of paste compositions for the oral administration of anthelmintic compositions is described in U.S. Pat. No. 3,746,490. The patent describes pastes of liquid dimethyl-2,2-dichlorovinyl phosphate (or DDVP) alone and contained in a polyvinyl chloride pellets.

Other anthelmintic paste compositions are described in U.S. Pat. No. 4,141,975, which describes an anthelmintic paste composition containing 0,0-dimethyl 1-hydroxy-2,2,2-trichloroethylphosphonate (Trichlorfon), and U.S. Pat. No. 4,277,467 which describes anthelmintic paste compositions containing trichlorfon and N-(2-methoxyacetamide-4-phenyl-thiophenyl)-N',N''-bis-methoxycarbonylquanidine (Febantel).

The use of 1-6-phenyl-2,3,5,6-tetrahydroimidazo[2,1-b]thiazole hydrochloride and trichlorfon, as a combination anthelmintic treatment, suitable for oral or parenteral administration is described in U.S. Pat. No. 3,937,825.

Previous attempts to prepare anthelmintic paste compositions containing two active ingredients such as the hydrochloride salt of dl-6-phenyl-2,3,5,6-tetrahydroimidazo[2,1-b]-thiazole or 1-6-phenyl-2,3,5,6-tetrahydroimidazo[2,1-b]thiazole, hereinafter referred to respectively as dl-tetramisole and l-tetramisole, with organophosphate anthelmintics such as trichlorfon, famphur, coumaphos, dimethoate, cythioate, chlorpyrifos, temephos and the like, resulted in paste compositions which exhibit physical instability overtime and at elevated temperatures. These pastes shrink and separate upon aging and at elevated temperatures, giving compositions which are non-homogeneous and unsuitable for use.

It has been found that physically stable anthelmintic paste compositions containing dl-tetramisole and l-tetramisole in combinations with other anthelmintics such as the organophosphate compounds described above may be prepared when resinated dl- or l-tetramisole is used to prepare the anthelmintic combination pastes. The resulting paste compositions comprising 2% to 24% on a weight basis of dl- or l-tetramisole resinate, 40% to 75% on a weight basis of heavy mineral oil, 0.0% to 2.5% on a weight basis of a nonionic surfactant, 0.0% to 31% on a weight basis of an organophosphate, 0.0% to 5.0% on a weight basis of barium sulfate, 2.0% to 10.0% on a weight basis of a fumed or precipitated silica, exhibit greatly improved physical stability over extended periods of time and at elevated temperatures in comparison to paste compositions prepared using acid salts such as the hydrochloride salt of dl- or l-tetramisole.

Resinated forms of dl-tetramisole and l-tetramisole suitable for use in preparing paste compositions of the invention are described in U.S. Pat. No. 3,574,227. U.S. Pat. No. 3,574,227 addresses the problems associated with the bitter taste of these anthelmintics and their chemical instability which can result in chemical degradation and loss of potency when combined in animal feedstuffs. It has been found that resinated forms of dl-tetramisole and l-tetramisole may be used to prepare physically stable paste compositions containing other active ingredients such as the organophosphate compounds described above which are not compatable with the acid addition salts of dl-tetramisole and l-tetramisole.

Strongly acidic resins are preferred in the invention compositions since they provide resinates in which the tetramisole is more strongly ionically bonded to the ion exchanged resin, thus substantially preventing ionization of the tetramisole. The preferred resins for the manufacture of the resinates of the invention are the strongly acidic resins including sulfonated polystyrenes prepared from styrene and from about 1 to about 20 weight percent of divinyl benzene which functions as a cross-linking agent. Examples of resins useful in the invention include AMBERLITE ® IR-120 and IR-112, and DOWEX ® 50 and 50W resins; sulfonated phenolic resins including AMBERLITE ®IR-1 resins; cellulose alkylsulfonic acid resins including Cellex SE resin; phenol methylene sulfonic acid resins including Acirolite C-131 resin; and sulfonated coal.

The reaction to form the tetramisole resinates can be carried out within a wide temperature range so long as the solvent remains fluid and is not evaporated in excessive amounts. For example, temperatures of about −50° C. to 150° C., and preferably between about 0° C. and 100° C. can be employed. Within the preferred temperature range, the reaction proceeds rapidly and loading of the resin is essentially complete. Generally 5 to 600,000 ppm, and preferably 100,000 to 300,000 ppm of the tetramisole compound are employed in the aqueous or organic solvent for use in the reaction.

The tetramisole solution can be contacted with the resin in any convenient manner such as passing the tetramisole solution through a resin bed or mixing the solution with finely divided resin particles. These particles are of a size between about 10 and 400 mesh and preferably 16 to 200 mesh. The molar ratio of tetramisole to resin employed is not critical and is usually within the range of 0.125:1 to 3:1, preferably 0.5:1 to 2:1. A ratio falling within the preferred range permits most efficient loading of the resin within a reasonable period of time. There is little advantage to employing a reactant ratio outside the broad range since there is no significant improvement in either the amount or rate of ion exchange obtained. The tetramisole resinates suitable for use in accordance with this invention contain from about 1% to 56% by weight of tetramisole, and may be used directly in the preparation of pastes or may be milled to a particle size of 40 to 350 mesh prior to use in preparing compositions of the invention.

The physically stable anthelmintic paste compositions of the invention may be prepared by admixing 40% to 75% on a weight basis of a heavy mineral oil with 0.5% to 2.5% on a weight basis of a nonionic sirfactant such as Polysorbate 20, 2% to 24% on a weight basis of milled (40, 50, 100 mesh), l-tetramisol resinate, 0% to 31% on a weight basis of another medicament such as the organophosphate compounds described above, 0% to 5% on a weight basis barium sulfate, and 2% to 10% on a weight basis of a colloidal silica, until homogeneous mixture is obtained. The resulting mixture is then homogenized in a homogenizer such as Eppenbach Homomixer, yielding the desired physically stable viscous paste.

Anthelmintic paste compositions of the invention containing dl- or l-tetramisole as a resinate may include a wide variety of other active ingredients such as antibiotics, vaccines, vitamins, mineral supplements or mixtures thereof may also be obtained. Examples of antibiotics are chlorotetracycline, sulfamethazine, sulfethoxypyridazine, sulfathiazole, tylosin or nitrofuran.

Throughout the test, the organophosphate compounds are referred to by generic names. A complete listing of the corresponding chemical names is given below.

Trichlorfon: 0,0-dimethyl 1-hydroxy-2,2,2-trichloroethylphosphonate
Famphur: 0,0-dimethyl 0-p-(dimethylsulfamoyl)phenyl phosphorothioate
Coumuphos: 0-(3-chloro-4-methyl-2-oxo-2H-benzopyran-7-yl) 0,0-diethyl phosphorothioate
Dimethoate: 0,0-dimethyl S-[2-(methylamino)-2-oxoethyl]phosphorodithioate
Cythioate: phenyl 0,0-dimethyl 0-p-sulfamoyl phosphorothioate
Chlorpyrifos: 0,0-diethyl 0-(3,5,6-trichloro-2-pyridyl)-phosphorothioate
Temephos: 0,0'-(thiodi-4,1-phenylene)bis(0,0-dimethyl phosphorthioate homogenized in a Homomixer, yielding the desired anthelmintic paste combination composition.

By utilizing the above procedure and substituting the appropriate components, the paste compositions summarized in Table I below may be prepared.

TABLE I

| Composition of Component | 1 % w/w | 2 % w/w | 3 % w/w | 4 % w/w | 5 % w/w | 6 % w/w | 7 % w/w | 8 % w/w | 9 % w/w | 10 % w/w |
|---|---|---|---|---|---|---|---|---|---|---|
| l-tetramisole HCl | 5.83 (5.75) | 5.83 (5.75) | 12.28 (11.72) | — | 40 mesh — | 100 mesh — | — | — | — | — |
| Resinate | — | — | — | 12.00* (5.75) | 12.0 (5.75) | 12.0 (5.75) | 12.0 (5.75) | 11.50 (5.75) | 11.50 (5.75) | 11.50 (5.75) |
| Famphur | 29.06 | — | — | — | 29.2* (28.47) | 29.2* (28.47) | 29.2* (28.47) | — | — | — |
| Trichlorfon | — | 29.06 | — | 30.00* (28.75) | — | — | — | 30.65* (40.0) | 30.81* (30.0) | 30.81* (30.0) |
| Polysorbate 20 | 1.0 | 1.0 | 1.01 | 1.50 | 0.7 | 1.10 | 1.50 | 1.50 | 1.50 | 1.50 |
| Colloidal silica | 2.75 | 2.75 | 3.55 | 2.90 | 3.00 | 2.75 | 2.75 | 3.23 | 3.23 | 3.23 |
| BaSO$_4$ | 5.00 | 5.00 | 10.15 | 5.00 | 5.00 | 5.00 | 5.00 | — | — | — |
| Heavy mineral oil | 56.36 | 56.36 | 72.99 | 48.6 | 50.1 | 49.95 | 49.55 | 53.116 | 52.96 | 52.96 |

*Premix containing 1% to 3% by weight of fumed silica from milling.
( ) Denotes % active ingredient, figuring for l-tetramisole expressed as HCl equivalent.

EXAMPLE 1

Polysorbate 20 60 g, 1.50% on a weight basis is added to heavy mineral oil 2164.64 g, 53.12% on a weight basis and the resulting mixture agitated in a Ross double planetary mixer for five minutes. 1-Tetramisole resinate 460 g, 11.50 on a weight basis is then added, after mixing for five minutes, a preblend, 1226 g, 30.65% on a weight basis, comprised of mixture of technical trichlorfon (96.2% pure) 97.5% by weight and fumed silica, 2.5% by weight which has been milled to a mean particle size of 62 microns is added. After blending for ten minutes fumed silica 3.23% on a weight basis is added and blending continued for 15 minutes. The resulting mixture is homogenized in a Homomixer, yielding the desired anthelmintic paste combination composition.

EXAMPLE 2

Physical stability of anthelmintic paste compositions

The physical stability of the anthelmintic paste compositions of the invention is evaluated by storing samples at 37° C. and 45° C. and visually inspecting the paste periodically for shrinkage or clear liquid formation.

The results of these experiments summarized in Table II below demonstrate the enhanced physical stability of anthelmintic paste compositions containing resinated l-tetramisole and organophosphate compounds compared to the control combinations which are prepared using the hydrochloride salt.

TABLE II

| Composition of Stability | 1 % w/w | 2 % w/w | 3 % w/w | 4 % w/w | 5 % w/w | 6 % w/w | 7 % w/w | 8 % w/w | 9 % w/w | 10 % w/w |
|---|---|---|---|---|---|---|---|---|---|---|
| 37° C. | | | | | | | | | | |
| 2 months | Separates | Separates | | | | | | | | |
| 3 months | | | | | | | | Stable | Stable | Stable |
| 6 months | | | | | Stable | Stable | Stable | | | |
| 45° C. | | | | | | | | | | |
| 1 months | Separates | Separates | | | | | | | | |
| 2 months | | | Stable | | | | | | | |
| 6 months | | | | Stable | Stable | Stable | Stable | | | |

What is claimed is:

1. A physically stable anthelmintic paste composition comprising 2% to 24% on a weight basis of resinated l-tetramisole or resinated dl-tetramisole, 40% to 75% on a weight basis of heavy mineral oil, 0..0% to 2.5% on a weight basis of a nonionic surfactant, 0.5% to 31.0% on a weight basis of an organophosphate compound, 0% to 5% on a weight basis of an agent to increase the density of the composition, and 2% to 10% on a weight basis of a fumed or precipitated silica.

2. A composition according to claim 1, wherein the organophosphate compound is famphur, trichlorfon, coumaphos, dimethoate, cythioate, chlorpyrifos, or temephos.

3. A composition according to claim 2, wherein the organophosphate compound is trichlorfon.

4. A composition according to claim 2, wherein the organophosphate compound is famphur.

5. A composition according to claim 2, containing 2% to 24% on a weight basis of resinated l-tetramisole and 2% to 31% on a weight basis of trichlorfon.

6. A composition according to claim 2, containing 2% to 24% on a weight basis of resinated l-tetramisole and 2% to 31% on a weight basis of famphur.

7. A composition according to claim 1, further comprising an antibiotic of chlorotetracycline, sulfamethazine, sulfethoxypyridazine, sulfathiazole, tylosin or nitrofuran.

8. A composition according to claim 1, further comprising a vaccine.

9. A composition according to claim 1, further comprising a vitamin, a mineral supplement or a mixture thereof.

10. A composition according to claim 1, wherein the agent to increase the density of the composition is barium sulfate.

* * * * *